United States Patent
Martin et al.

(10) Patent No.: US 9,063,203 B2
(45) Date of Patent: Jun. 23, 2015

(54) METHOD FOR DETERMINING AT LEAST ONE PET PARAMETER

(75) Inventors: Diana Martin, Herzogenaurach (DE); Wolfgang Bielmeier, Nürnberg (DE)

(73) Assignee: SIEMENS AKTIENGESELLSCHAFT, Munich (DE)

(*) Notice: Subject to any disclaimer, the term of this patent is extended or adjusted under 35 U.S.C. 154(b) by 1341 days.

(21) Appl. No.: 12/153,557

(22) Filed: May 21, 2008

(65) Prior Publication Data
US 2008/0319305 A1      Dec. 25, 2008

(30) Foreign Application Priority Data

May 22, 2007   (DE) .......................... 10 2007 023 655

(51) Int. Cl.
| | | |
|---|---|---|
| A61B 5/055 | (2006.01) | |
| G01R 33/48 | (2006.01) | |
| A61B 6/03 | (2006.01) | |
| A61B 6/00 | (2006.01) | |
| G01T 1/16 | (2006.01) | |
| A61B 6/02 | (2006.01) | |
| G01T 1/161 | (2006.01) | |
| G01R 33/54 | (2006.01) | |

(52) U.S. Cl.
CPC .............. *G01R 33/481* (2013.01); *A61B 6/037* (2013.01); *A61B 6/545* (2013.01); *G01T 1/1603* (2013.01); *A61B 6/5247* (2013.01); *G01R 33/543* (2013.01)

(58) Field of Classification Search
CPC ...... A61B 6/037; A61B 6/545; A61B 6/5247; G01R 33/481; G01R 33/543; G01T 1/1603
USPC ........................................................ 250/363.04
See application file for complete search history.

(56) References Cited

U.S. PATENT DOCUMENTS

| | | | |
|---|---|---|---|
| 6,490,476 B1 * | 12/2002 | Townsend et al. ............. | 600/427 |
| 7,180,074 B1 * | 2/2007 | Crosetto ................... | 250/370.09 |
| 7,447,345 B2 * | 11/2008 | Shanmugam et al. ......... | 382/131 |
| 7,518,114 B2 * | 4/2009 | Ganin et al. .............. | 250/363.03 |
| 7,650,021 B2 * | 1/2010 | Braess ........................... | 382/128 |

(Continued)

FOREIGN PATENT DOCUMENTS

DE   102005015070 A1   10/2006

OTHER PUBLICATIONS

Beer et al. "PET-Based Human Dosimetry of 18F-Galacto-RGD, a New Radiotracer for Imaging a vb3 Expression." J Nucl Med. 2006; 47:763-769.*

(Continued)

*Primary Examiner* — Long V Le
*Assistant Examiner* — Angela M Hoffa
(74) *Attorney, Agent, or Firm* — Harness, Dickey & Pierce, P.L.C.

(57) ABSTRACT

A method is disclosed for determining at least one PET parameter for a PET examination in a combined magnetic resonance/PET scanner designed for isocentric measurement. In at least one embodiment, at least one acquisition time for the PET examination is determined as a PET parameter from magnetic resonance data, recorded for determining patient-specific examination parameters for a magnetic resonance examination, and/or from at least one patient-specific information value derived therefrom, and is displayed and/or used for controlling the scanner.

16 Claims, 1 Drawing Sheet

(56) References Cited

U.S. PATENT DOCUMENTS

| | | |
|---|---|---|
| 2005/0129295 A1* | 6/2005 | Shanmugam et al. ........ 382/131 |
| 2006/0004275 A1 | 1/2006 | Vija et al. |
| 2006/0052685 A1 | 3/2006 | Cho et al. |
| 2006/0097175 A1* | 5/2006 | Ganin et al. ............. 250/363.03 |
| 2006/0251312 A1 | 11/2006 | Krieg et al. |
| 2007/0102641 A1 | 5/2007 | Schmand et al. |
| 2008/0146914 A1* | 6/2008 | Polzin et al. .................. 600/420 |
| 2008/0164875 A1* | 7/2008 | Haworth et al. .............. 324/318 |

OTHER PUBLICATIONS

Habib Zaidi et al; Magnetic resonance imaging-guided attenuation and scatter corrections in three-dimensional brain positron emission tomography; Med.Phys. 30 (5), May 2003, S. 937-948; Others.

German Patent Office Action dated Aug. 13, 2008.

* cited by examiner

METHOD FOR DETERMINING AT LEAST ONE PET PARAMETER

PRIORITY STATEMENT

The present application hereby claims priority under 35 U.S.C. §119 on German patent application number DE 10 2007 023 655.9 filed May 22, 2007, the entire contents of which is hereby incorporated herein by reference.

FIELD

Embodiments of the invention generally relate to a method for determining at least one PET parameter for a PET examination in a combined magnetic resonance/PET scanner designed for isocentric measurement.

BACKGROUND

A multiplicity of parameters which control the sequence of the examination and also its evaluation are required for nuclear medicine examinations such as PET (positron emission tomography). The acquisition time, in particular, that is to say the time throughout which nuclear medicine data are acquired, needs to be mentioned in this context. The acquisition time, that is to say the length of time of data acquisition, depends strongly on the respective patient or the corresponding examination volume, since the attenuation of the radioactive radiation within the detector region is taken into account. By way of example, in the abdominal region in a longer acquisition time must be planned for heavy patients than for thin patients. Analogously, a shorter acquisition time is possible in the region of the extremities than in the abdomen. Since it is protected by the skull bone, longer acquisition times are also required in the head region.

Until now, in the case of nuclear medicine examinations it has been common to let the user input the acquisition time on the basis of his experience. Here, the acquisition time can be input as a fixed period of time or as a number of events to be detected. However, such a procedure is prone to the error inherent in the user input. More experienced users will achieve a better setting and thus a better data quality on account of their larger wealth of knowledge, but even in their case input errors can happen.

In recent times, so-called hybrid modalities have been proposed in medical imaging. In the case of such a combination, a modality with a high spatial resolution (magnetic resonance tomography or computed tomography) is usually combined with a modality with a high sensitivity (nuclear medicine modality, such as SPECT (single photon emission computed tomography) or PET). A particularly promising variant of such a combined scanner is the combination of magnetic resonance tomography with PET (positron emission tomography) since, for example, many functional examinations require a combination of the image data of these modalities.

SUMMARY

In at least one embodiment of the invention, a method is specified for determining at least one PET parameter which allows automated setting of the acquisition time as a PET parameter and which is matched to the patient to be examined and the region to be examined.

In at least one embodiment of the invention, at least one acquisition time for the PET examination, determined from magnetic resonance data recorded for determining patient-specific examination parameters for a magnetic resonance examination and/or at least one patient-specific information value derived therefrom, are/is determined and displayed as a PET parameter and/or used to control the scanner.

In the case of conventional magnetic resonance scanners it is already known that magnetic resonance data is recorded prior to the actual magnetic resonance examination by way of example in the form of a so-called localizer, by means of which patient-specific examination parameters are then derived for the magnetic resonance examination. Particularly with regard to limit values of the SAR (specific absorption rate) exposure, it is common to undertake such pre-recordings. In addition, the target area of interest can be localized if, for example, a fast full-body recording, that is to say a full-body overview image, is recorded as magnetic resonance data. In particular, patient-specific information values can also be extracted from the magnetic resonance data in addition to the SAR, for example the size of the patient or his various physical dimensions and weight. To determine the SAR, the absorption of the radio-frequency power, the exposed body regions (head, torso, extremities) and their masses are for example determined from the magnetic resonance data. In this case, the absorbed radio-frequency power is proportional to the exposed mass.

According to at least one embodiment of the invention, it has now been found that the magnetic resonance data recorded during such a pre-examination can also supply relevant data for setting the acquisition time for a PET examination. This holds in particular since an isocentric measurement can be carried out using the combined magnetic resonance/PET scanner; this means that, for example, the mass distribution derived from the magnetic resonance data in the field of view of the magnetic resonance modality can be transferred without problems to the field of view of the PET modality (which is generally the same). Considering the magnetic resonance data and/or at least one patient-specific information value derived therefrom, an acquisition time is accordingly determined in accordance with the invention which is ideally matched to the actually examined target volume. The magnetic resonance data is thus particularly advantageously used for two purposes, and the integration of the modalities in the combined magnetic resonance/PET scanner is increased. This results in higher quality PET data being achieved. The cumbersome and error-prone manual input empirical values of acquisition times is thus dispensed with.

In particular, at least one embodiment of the present invention can also determine different acquisition times for different areas in the case of full-body examinations. In this manner, the acquisition time of the head by the PET modality can be increased automatically on account of the high attenuation, and be decreased in the extremities. The acquisition time of the PET examination is accordingly increased for heavy patients compared to thin patients, and unusual mass distributions can also be taken into account.

In addition, further PET parameters can also be determined, taking into account the magnetic resonance data and/or the at least one information value derived therefrom. These can be examination-relevant parameters, for example the tracer to be used and/or the required tracer dose and/or triggering parameters and/or gating parameters, and additionally or alternatively also evaluation-relevant PET parameters, in particular reconstruction parameters. In particular, the whole PET parameter space can be determined or matched taking into account the magnetic resonance data or the information value or values.

By way of example, the SAR and/or the volume and/or the mass of the patient and/or a part of the patient located in the examination area can be used as an information value or values. By way of example, the most useful basis has proved to be the (spatially resolved) SAR, which is determined in any case. The volume or mass information of the patient, which can be derived from the magnetic resonance data, can advantageously be used to determine the acquisition time and further PET parameters, if applicable.

Further patient-specific values, in particular the age and/or sex and/or the target volume of interest, can additionally be incorporated into determining the PET parameter or parameters. By way of example, these can be determined from an electronic patient record and/or a measurement record and/or can be entered by a user. All the data required for determining an optimal acquisition time are correspondingly particularly advantageously available.

In order to be able to determine an acquisition time from the information, two embodiments are substantially feasible. On the one hand, the magnetic resonance data and/or the information value and/or the further patient-specific data can be linked to the PET parameter or parameters by means of a look-up table. By way of example, specific PET parameters, in particular acquisition times, are associated in such a table with specific intervals of the magnetic resonance data and/or the information value or values and/or the further patient-specific data. This can then be queried from at least one storage device by a control device for the magnetic resonance/PET scanner carrying out the method and can, for example, be used directly for controlling the magnetic resonance/PET scanner. In the simplest case of the method, different SAR values are respectively assigned an acquisition time. However, the more data that is considered, the more exact the setting becomes and the higher the quality of the PET examination will be.

Alternatively, or in addition, the magnetic resonance data and/or the information value and/or the further patient-specific data can be linked to the PET parameter or parameters by way of a formula. By way of example, the results of calibration measurements can be used to determine such a functional dependence, and can also, incidentally, serve as the basis for the abovementioned look-up table.

As has already been mentioned, the magnetic resonance data can be recorded by a fast full-body MRI scan, in particular a localizer recording. In this case the entire patient is recorded at low resolution, which nevertheless suffices for being able to determine his physical extent, mass values and thus his SAR. Moreover, the exact position of the target volume can be determined from such a full-body measurement. In a first embodiment of the method, only a coronal or sagittal slice, that is to say two-dimensional data, is in this case recorded as magnetic resonance data. However, it makes more sense to record three-dimensional magnetic resonance data in order to obtain information about the whole patient. Then, data is also available in all spatial directions.

In addition to the method, at least one embodiment of the invention also relates to a medical examination device comprising a combined magnetic resonance/PET scanner with a control device designed for carrying out the method in accordance with at least one embodiment of the present invention. For this purpose, the control device can derive patient-specific information values from the magnetic resonance data. Moreover, the control device is designed for the purpose of determining at least one acquisition time for the PET examination as a PET parameter from the magnetic resonance data and/or at least one patient-specific information value derived therefrom. Should such a scanner have a monitor and an input apparatus, it is sensible in any case to display the determined PET parameter or parameters there. If automatic control is not provided, the parameters can still be processed and/or confirmed by a user. Otherwise, the control device is designed for direct control of the magnetic resonance/PET scanner on the basis of the determined PET parameters—after confirmation by the user, if applicable.

BRIEF DESCRIPTION OF THE DRAWINGS

Further advantages and details of the present invention result from the example embodiments described below and from the drawings, in which.

DETAILED DESCRIPTION OF THE EXAMPLE EMBODIMENTS

Figure 1:
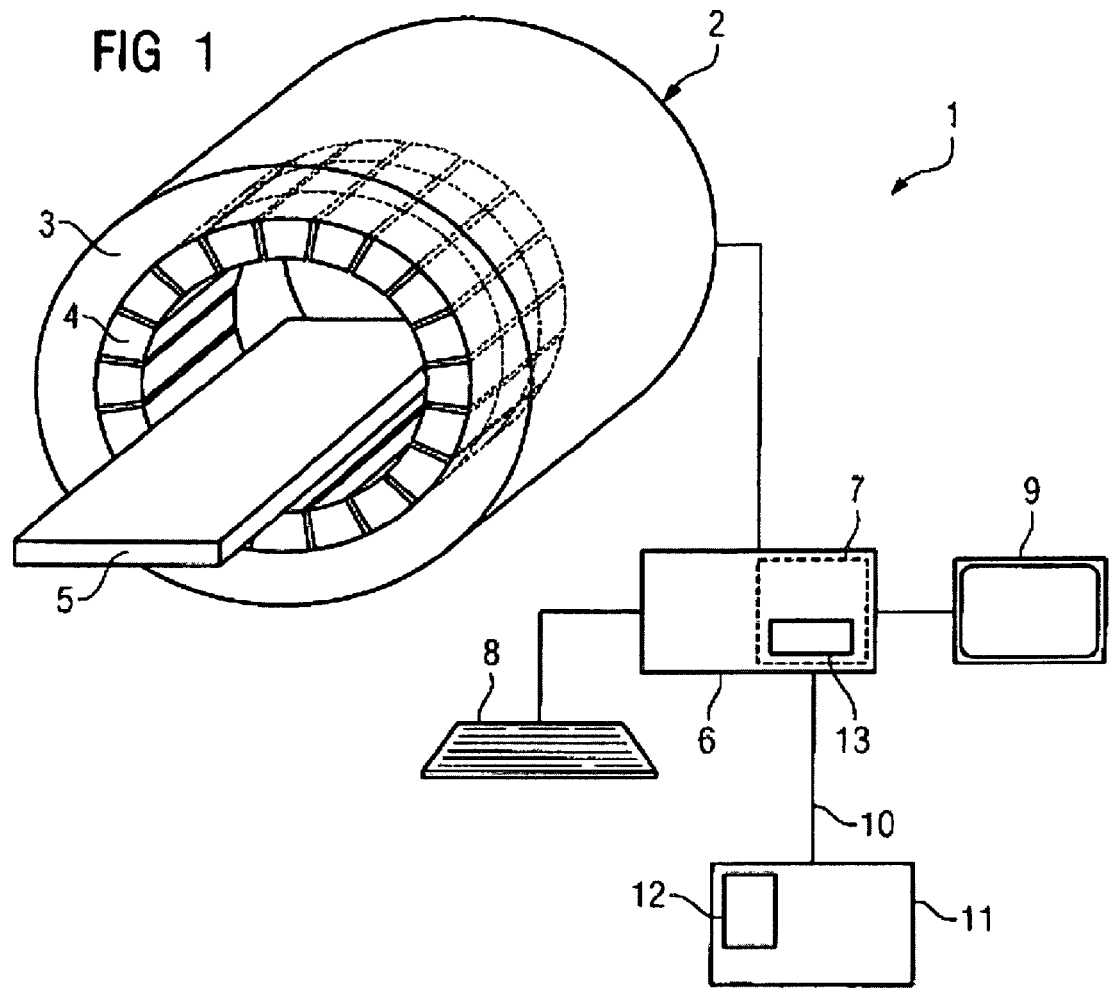
FIG. 1 shows a combined magnetic resonance/PET scanner according to an embodiment of the invention and FIG. 2 shows a flowchart of the method according to an embodiment of the invention.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows an outline sketch of a medical examination device 1 according to an embodiment of the invention. This includes a combined magnetic resonance/PET scanner 2, which comprises a solenoid magnet 3, as well as gradient coils and radio-frequency coils (not shown) for recording magnetic resonance data. A PET detector 4 is provided within the magnet 3, for recording PET measurement data. A patient opening is defined by the magnet 3 and the PET detector 4, into which a patient on a patient couch 5 can be inserted in order to be able to undertake a functional examination, for example.

The medical examination device 1 furthermore has a control device 6, which may have at least one storage device 7. The control device 6 controls the recording operation and the evaluation operation of the scanner 2. The input device 8, for example a keyboard, and a monitor 9 are connected to the control device 6. Using the input device 8, parameters for recording, in particular a measurement protocol, and for evaluation, in particular reconstruction parameters and fusion parameters, can for example be entered and edited. Further relevant data for recording and evaluation operation can be supplied from external computation devices 11, on which the electronic patient records 12 are stored, for example, via a communication link 10.

Incidentally, isocentric recording of magnetic resonance data and PET data is possible by way of the medical examination device 1.

By way of example, a look-up table 13 can be stored in the at least one storage device 7, and relates the magnetic resonance data from a pre-examination (which is carried out for determining examination parameters for the actual magnetic resonance examination), and/or at least one patient-specific information value derived therefrom, to one or more PET parameters, in particular, however, the acquisition time for a PET examination. The control device 6 is furthermore designed to carry out the method according to the invention, which means it can determine at least one PET parameter for a PET examination, in particular, however, the acquisition time for a PET examination, and display it on the monitor 9 and use it to control the scanner 2, taking the magnetic resonance data and/or the patient-specific information value or values derived therefrom into account.

Figure 2:
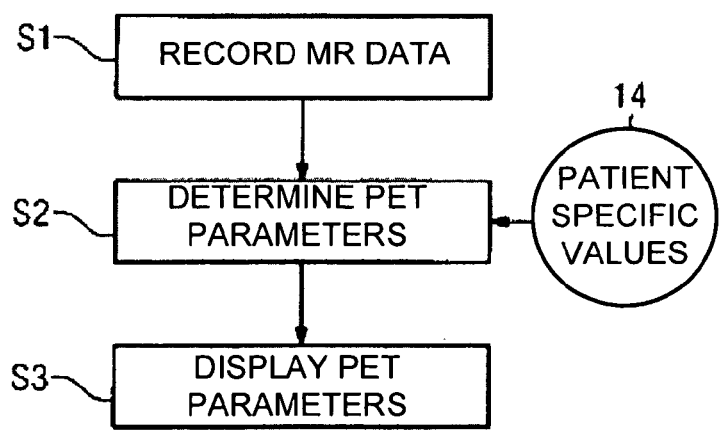

FIG. 2 shows a flowchart of an embodiment of the inventive method.

First of all, magnetic resonance data is recorded in a step S1 within the course of a pre-examination, and is used for determining examination parameters for a magnetic resonance examination. By way of example, in this case, these can be so-called localizer recordings; however, a full-body recording is advantageously recorded as magnetic resonance data. This can be two-dimensional, that is to say it may include a coronal and/or sagittal section, or else it may be a complete three-dimensional full-body recording comprising a plurality of slices. In this case, three-dimensional magnetic resonance data is preferred, since a greater, in particular complete, number of items of information can be derived from it.

One or more patient-specific information values are now usually determined therefrom. These relate to, for example, the volume and/or the mass of the patient, in particular also relating to specific regions of his body. The specific absorption rate (SAR) of the patient can be derived therefrom. There are limit values for the SAR which must be observed during magnetic resonance examinations.

PET parameters comprising the acquisition time for a PET examination are now determined therefrom in the step S2. By way of example, the acquisition time in the abdominal region in the case of heavy patients must be increased on account of the greater radiation screening. However, further PET parameters can also be determined in addition to the acquisition time. By way of example, it is thus feasible to determine further examination-relevant PET parameters, for example the tracer to be used and/or the required tracer dose and/or triggering parameters and/or gating parameters, and also evaluation-relevant parameters, for example reconstruction parameters, as a function of the magnetic resonance data and/or the information value or values. By way of example, the look-up table 13 can be used to link the magnetic resonance data or the information value or values to the acquisition time and the further PET parameters if appropriate, and is stored in the storage means 7. However, a functional relationship in the form of a formula can be used just as well.

Expediently, further patient-specific values 14 can also be included in the determination of the PET parameter or parameters, for example the age of the patient or the patient's sex. By way of example, these can be determined from an electronic patient record 12. Of course, is also possible that those values can just as well be deduced from a measurement record or user input. In addition to the age and the sex of the patient, the target volume of interest is usually also useful for determining the acquisition time.

Finally, in step S3, the PET parameters are displayed, for example on the monitor 9. There, they can still be processed or confirmed by a user via the input device 8, for example. The scanner 2 is then controlled for carrying out the PET examination, taking the determined PET parameters into account. Of course it is also possible to use the determined PET parameter or parameters directly for controlling the combined magnetic resonance/PET scanner 2, without additional user interaction.

If the magnetic resonance/PET scanner 2 is also designed for simultaneously recording the magnetic resonance data and the PET data, then the control device 6 can also control the scanner for simultaneous recording, in accordance with the PET parameters and the examination parameters, for the magnetic resonance examination. In the case of the method according to an embodiment of the invention, all of these parameters were advantageously determined and set as a function of the magnetic resonance pre-examination.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for controlling a position emission tomography (PET) examination in a combined magnetic resonance/PET scanner designed for isocentric measurement, the method comprising:
   recording magnetic resonance data with the combined magnetic resonance/PET scanner;
   deriving patient-specific information from the magnetic resonance data, wherein the patient specific information includes a specific absorption rate;
   determining PET parameters from the specific absorption rate, wherein the PET parameters include at least one acquisition time for the PET examination; and
   controlling the combined magnetic resonance/PET scanner to perform the PET examination with the determined PET parameters.

2. The method as claimed in claim 1, wherein the patient-specific information further includes at least one of a volume, a mass of the patient and a mass of a part of the patient located in the examination area.

3. The method as claimed in claim 1, wherein the PET parameters further include at least one PET parameter, which is determined as a function of a target volume of interest.

4. The method as claimed in claim 3, wherein the patient-specific information further includes the target volume of interest.

5. The method as claimed in claim 3, wherein at least one of the magnetic resonance data and the patient-specific information are linked to the PET parameters via a look-up table.

6. The method as claimed in claim 3, wherein at least one of the magnetic resonance data and the patient-specific information are linked to the PET parameters via a formula.

7. The method as claimed in claim 1, wherein at least one of the magnetic resonance data and the patient-specific information are linked to the PET parameters via a look-up table.

8. The method as claimed in claim 1, wherein at least one of the magnetic resonance data and the patient-specific information are linked to the PET parameters via a formula.

9. The method as claimed in claim 1, wherein the magnetic resonance data is recorded by a fast full-body measurement by way of magnetic resonance.

10. The method as claimed in claim 9, wherein only a coronal or sagittal section is recorded as the magnetic resonance data.

11. The method as claimed in claim 9, wherein three-dimensional magnetic resonance data are recorded.

12. A medical examination device, comprising:
    a combined magnetic resonance/PET scanner with a control device, the control device being configured to carry out the method as claimed in claim 1.

13. A tangible computer readable medium including program segments for, when executed on a computer device, causing the computer device to implement the method of claim 1.

14. A medical examination device, comprising:
    a combined magnetic resonance/positron emission tomography (PET) scanner including,
        means for recording magnetic resonance data with the combined magnetic resonance/positron emission tomography (PET) scanner;
        means for deriving patient-specific information from the magnetic resonance data, wherein the patient specific information includes a specific absorption rate;
        means for determining PET parameters from the specific absorption rate, wherein the PET parameters include at least one acquisition time for the PET examination; and
        means for controlling the combined magnetic resonance/PET scanner to perform the PET examination with the determined PET parameters.

15. The medical examination device as claimed in claim 14, wherein the patient-specific information further includes at least one of a volume, a mass of the patient and a mass of a part of the patient located in the examination area.

16. A medical examination device, comprising:
    a combined magnetic resonance/positron emission tomography (PET) scanner including a control device configured to perform the steps of,
        recording magnetic resonance data with the combined magnetic resonance/PET scanner;

deriving patient-specific information from the magnetic resonance data, wherein the patient specific information includes a specific absorption rate;

determining PET parameters from the specific absorption rate, wherein the PET parameters include at least one acquisition time for the PET examination; and controlling the combined magnetic resonance/PET scanner to perform the PET examination with the determined PET parameters.

\* \* \* \* \*